US006972111B1

(12) United States Patent
Kunisch et al.

(10) Patent No.: US 6,972,111 B1
(45) Date of Patent: Dec. 6, 2005

(54) ROSIN AMINE ANTI-FOULING AGENTS

(75) Inventors: Franz Kunisch, Odenthal (DE); Martin Kugler, Leichlingen (DE); Jean-Claude Braekman, Rhode Saint Genese (BE); Mark Plehiers, Brussels (BE); Gabriele Ferrari, Den Helder (NL); Marcel Vos, Huizen (NL)

(73) Assignees: Bayer Aktiengesellschaft, Leverkusen (DE); Universite Libre de Bruxelles, Bruxelles (BE); Nederlandse Organisatie Voor Toegepast, Eindhoven (NL); Natuurweten-schappelijk Onderzoek & Sigma Coatings, Uithoorn (NL)

( * ) Notice: Subject to any disclaimer, the term of this patent is extended or adjusted under 35 U.S.C. 154(b) by 0 days.

(21) Appl. No.: 09/936,124

(22) PCT Filed: Mar. 10, 2000

(86) PCT No.: PCT/EP00/02118

§ 371 (c)(1),
(2), (4) Date: Jan. 9, 2002

(87) PCT Pub. No.: WO00/55117

PCT Pub. Date: Sep. 21, 2000

(30) Foreign Application Priority Data

Mar. 16, 1999 (EP) ............................ 99105349

(51) Int. Cl.$^7$ ............................................. B08B 17/00
(52) U.S. Cl. .................... 422/6; 106/18.32; 106/18.33; 106/18.35; 523/122
(58) Field of Search ....................... 422/6, 28; 106/16, 106/18.32, 18.33, 18.35; 523/122

(56) References Cited

U.S. PATENT DOCUMENTS 5,236,493 A * 8/1993 Hunter et al. ................. 106/16

FOREIGN PATENT DOCUMENTS

| EP | 0 364 271 | 4/1990 |
| EP | 0 473 004 | 3/1992 |
| EP | 0 877 061 | 11/1998 |
| JP | 63017806 A2 * | 1/1988 |
| WO | 91/15546 | 10/1991 |

OTHER PUBLICATIONS

CAS Registry #35928-32-6.*
CAS Registry #73757-72-9.*
CAS Registry #115269-93-7.*
Methoden Der Organischen Chemie (Houben-Weyl) vol. E4 (month unavailable) 1983 pp. 352-357 U. Peterson aus Isocyanaten bzw. Alkalimetallcyanaten.
Methoden Der Organischen Chemie (Houben-Weyl) vol. 11/2 (month unavailable) 1958 pp. 74-85 G. Pieper Umwandlung von primaren und sekundaren Aminen.
Tetrahedron Letters vol. 22, pp 299-302 (month unavailable) 1981.
E. J. Corey and Shun-ichi Hashimoto A Practical Process for Large-Scale Synthesis of (S)-5-Hydroxy-6-Trans-8, 11, 14-CIS-Eicosatetranenoic Acid (5-Hete).
Tetrahedron Letters, vol. 30, No. 7, pp 845-846, (month unavailable) 1989.
Tomihiko Ohsawa, Naoki Mitsuda, Jun'ichi Nezu, Takeshi Oishi Dissolving Metal Reduction with crown ether—Reductive removal of isocyano groups.
Chem. Rev. vol. 72 (month unavailable) 1972 pp. 457-460 Shoichiro Ozaki Recent Advances in isocyanate chemistry and its implications in coatings.
Progress in Organic Coatings, 20(month unavailable) 1992 pp. 139-167 Gang-Fung Chen Developments in the field of rosin chemistry and its implications in coatings.
Chem. Pharm. Bull., vol. 33, (month unavailable) 1985 pp. 1472-1487, Hiroshi Wada.
Shin-Ichi Kodato, Masatoshi Kawamori, Tamio Morikawa, Hideo Nakaim Mikio Takeda, Seiichi Saito, Yuichi Onoda and Hajime Tamaki Antiulcer Activity of Dehydroabietic Acid Derivatives.
Can. J. Chem., vol. 41, (month unavailable) 1963 pp. 834-836 Richard F. Stockel The Preparation of Dehydroabietane-1-amine.
Houben-Weyl, vol. 8, 1952, 137-140.
Houben-Weyl vol. 11/2, 1958, 27-37.
Ungerer, Chem.Ind. 1985, 37, 730-732.
Williams, Antifouling Marine Coatings, Noyes Park Ridge, 1973.
Brian E. Cross et al, Preparation of the 15, 6alpha-lactone from 8 beta, 13 beta-tetrahydroabiectic acid, Journal of the Chemical Society, Perkin Transactions 1, vol. 12, 1981, pp. 3158-3160, XP002100081, p. 3158.
Rane D.S. et al: "New Strategies for the Hofman Reaction" Journal of Chemical Technology and Biotechnology (International Journal of Biotechnical and Chemical Processes). vol. 59, No. 3, Mar. 1, 1994.
CAS #63692-75-1, Prior Art.
CAS 121282 63-1, Prior Art.

* cited by examiner

Primary Examiner—Elizabeth McKane
(74) Attorney, Agent, or Firm—Marina V. Schneller; Venable LLP

(57) ABSTRACT

The invention relates to new and known compounds as well as methods for preventing the attachment of aquatic organisms to surfaces which are submerged for extensive periods of time in water. More particularly, this invention relates to the protection of submerged surfaces with new isonitrile, formamide, isocyanate and isothiocyanate anti-fouling agents.

16 Claims, No Drawings

ROSIN AMINE ANTI-FOULING AGENTS

FIELD OF INVENTION

The invention relates to new and known compounds as well as methods for preventing the attachment of aquatic organisms to surfaces which are submerged for extensive periods of time in water. More particularly, this invention relates to the protection of submerged surfaces with new isonitrile, formamide, isocyanate and isothiocyanate anti-fouling agents.

BACKGROUND OF THE INVENTION

The ever recurring growth of fouling organisms on underwater structures such as ships, docks, piers, pilings, fishnets, heat exchangers, dams, piping structures, intake screens, cooling towers and the like is a costly and hazardous problem in both marine and freshwater endeavors. The presence of fouling organisms such as barnacles, zebra mussels, algae, diatoms, hydroids, bryozoa, ascidians, tubeworms, Asiatic clams and the like causes economic damage in various ways: for example, attachment to the hulls of ships reduces fuel efficiency and causes loss of profitable sailing time because of the need to clean the hulls. Similarly, the attachment of these organisms to cooling water equipment decreases heat conductivity which eventually reduces or block the cooling power of the equipment and drives up cost.

A variety of agents useful for controlling fouling organisms in fresh water or sea water have been used to prevent the attachment and overgrowth of these organisms. A common method of controlling the presence or attachment of fouling organisms is to coat or permeate the underwater structure with a composition which comprises mixtures of toxic compounds such as tri-n-butyl tin or copper compounds. Anti-fouling agents in the form of a paint can contain up to 60% by weight of the active ingredients and can be used to paint surfaces such as the hull of ships. The paint prevents attachment and growth of fouling organisms by continuously releasing anti-fouling agents underwater. The disadvantage of many of the present anti-fouling agents is that they are persitant in the environment, are often acutely toxic and degrade too slowly in aquatic environments and are, therefore, ecologically harmful. Hazardous anti-fouling agents can eventually bioaccumulate and enter the food chain and therefore represent a threat to marine and human life.

For example, it is well established that heavy metal compounds, especially organotin compounds that are widely used as anti-fouling agents, accumulate in mussels.

It is an object of this invention to provide an environmentally and ecologically sound method of combatting or controlling marine and freshwater fouling organisms.

It is another object of this invention to provide an effective method for protecting aquatic structures against fouling by marine or freshwater fouling organisms.

It is a further object of this invention to provide antifoulant compositions which comprises certain derivatives of rosin compounds as the active agents.

SUMMARY OF THE INVENTION

The present invention provides new and known compounds and a method to prevent settlement on surfaces by marine or freshwater fouling organism which comprises contacting said organism or the locus thereof with an anti-fouling-effective amount of at least one compound of formula I1–I13 formula I1–I13

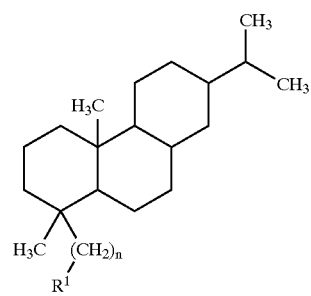

I1

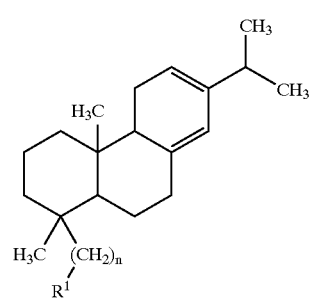

I2

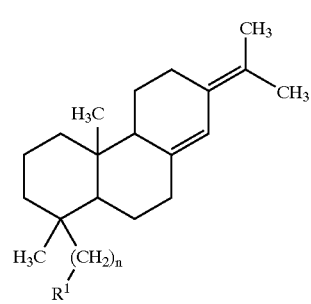

I3

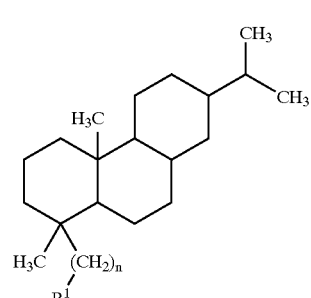

I4

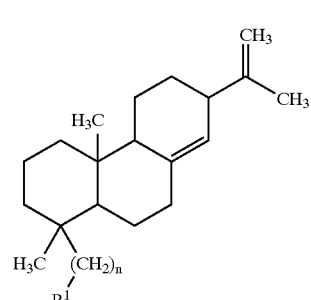

I5

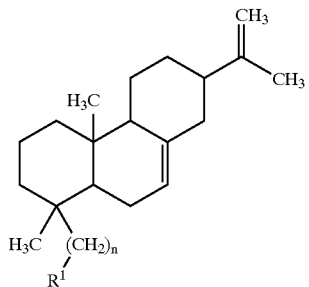

I6

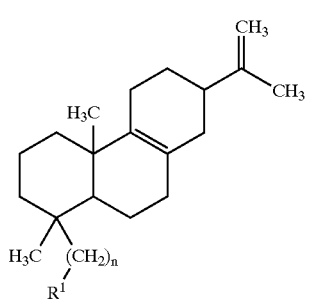

I7

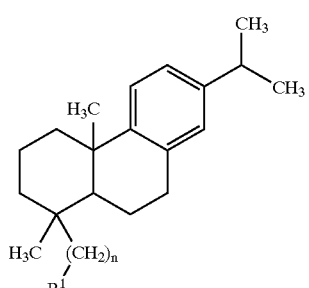

I8

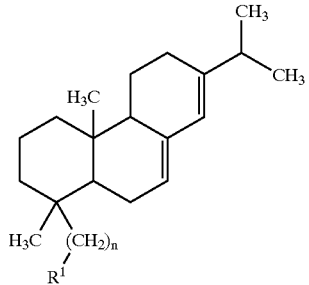

I9

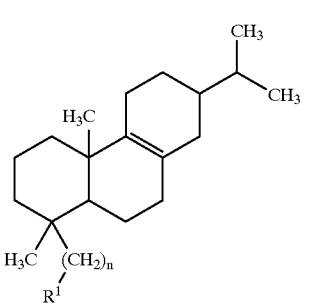

I10

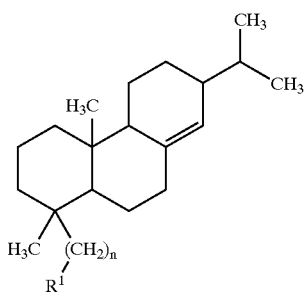

I11

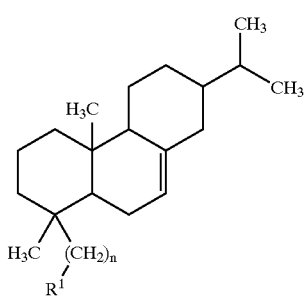

I13 wherein
R¹ represents NR²R³ wherein
  R² represents a hydrogen atom, C1–C8-alkyl and
  R³ represents C=OR⁴ wherein
    R⁴ represents a hydrogen atom or one of the groups OR⁵ or NHR⁵ wherein
      R⁵ designates C1–C8-alkyl or aryl, each optionally substituted by halogen; or
R¹ represents N=CR⁶R⁷ wherein
  R⁶ represents a hydrogen atom, C1–C6-alkyl or aryl, and
  R⁷ represents C1–C6-alkyl or aryl, each optionally substituted by halogen; or
R¹ represents an isonitrile, isocyanate, isothiocyanate or a guanidino group; and
n represents 0 or 1.

In the specification and claims the term:
halogen has the meaning of Cl, Br, I or F;
alkyl has the meaning of straight-chain or branched alkyl with 1 to 8, preferably 1 to 4 carbon atoms;
aryl has the meaning of aromatic, mono- or polycyclic hydrocarbon rings such as for example and preferred: naphthyl, anthranyl, phenanthryl, especially phenyl.

Preferred are compounds of formula I1–I13 wherein
R¹ represents NR²R³ wherein
  R² represents a hydrogen atom or C1–C4-alkyl and
  R³ represents C=OR⁴ wherein
    R⁴ represents a hydrogen atom or one of the groups OR⁵ or NHR⁵ wherein
      R⁵ represents C1–C4-alkyl or aryl, each optionally substituted by halogen; or
R¹ represents N=CR⁶R⁷ wherein
  R⁶ represents a hydrogen atom, methyl or optionally halogen substituted aryl, and
  R⁷ represents C1–C4-alkyl or optionally halogen substituted aryl; or R[1] represents an isonitrile, isocyanate, isothiocyanate or guanidino moiety.

Especially preferred are compounds of formula I1–I13 wherein
R[1] represents NR[2]R[3] wherein
R[2] represents a hydrogen atom and
R[3] represents C=OR[4] wherein
R[4] represents a hydrogen atom.

Especially preferred are also compounds of formula I1–I13 wherein
R[1] represents NR[2]R[3] wherein
R[2] represents a hydrogen atom and
R[3] represents C=OR[4] wherein
R[4] represents OR[5] or NHR[5] wherein
R[5] represents methyl, ethyl, n- or i-propyl or n-, s-, i- or t-butyl, or phenyl which is optionally substituted by halogen.

Especially preferred are also compounds of formula I1–I13 wherein
R[1] represents N=CR[6]R[7] wherein
R[6] represents methyl, ethyl, n- or i-propyl, n-, s-, i- or t-butyl, or preferred a hydrogen atom or and
R[7] represents methyl, ethyl, n- or i-propyl, n-, s-, i- or t-butyl or phenyl.

Especially preferred are also compounds of formula I1–I13 wherein
R[1] represents an isonitrile, isocyanate, isothiocyanate or guanidino moiety.

Preferred are compounds wherein n represents 1.

Preferred are Compounds of the Formula I8

The aforementioned compounds are accessible by standard procedures of organic chemistry which can be adopted to the Rosin moiety. The starting Rosin derived from Tall Oil, Gum or Wood is commercially available; for example Rosin amine as Hercules® Amine D. An overview on the different isomers of abietic acid as well as their preparation is given by Gang-Fung Chen in *Progress in Organic Coatings* 20, 1992, 139–167. In the following general schemes the synthesis of the different Rosin amine derivatives is outlined. For reasons of simplification, the synthesis routes are outlined for substructure I8 with n=1. The reaction sequences can be adopted easily to the other pure isomers and rosin oxidation/reduction products and also to mixtures of them.

Scheme 1

Compounds of formula I8 are accessible via acylation of Rosin amine with a chloro-formic-ester in an inert solvent with a base as HCl acceptor (see: Houben-Weyl Vol. 8, 1952, 137–140; ibid. Vol. 11/2, 1958, 27–37).

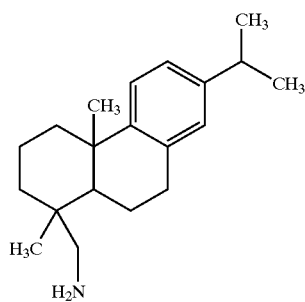

Rosin amine

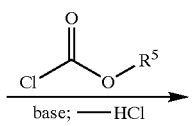

base; —HCl

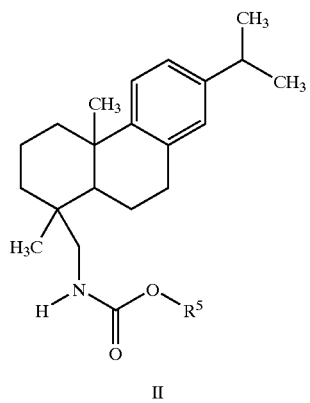

II

Scheme 2

Ureas of formula III can be synthesized by reacting Rosin amine with an isocyanate in an inert solvent (benzene, toluene, hydrocarbons etc.); see: Houben-Weyl Vol. E4, 1983, 352–357 or alternatively via reaction of Rosin isocyanate (s. below) with an aliphatic or aromatic amine.

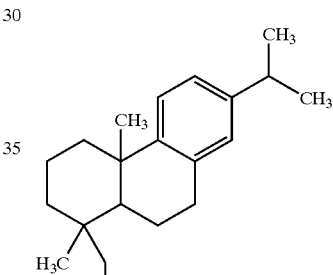

Rosin amine

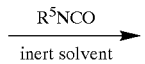

inert solvent

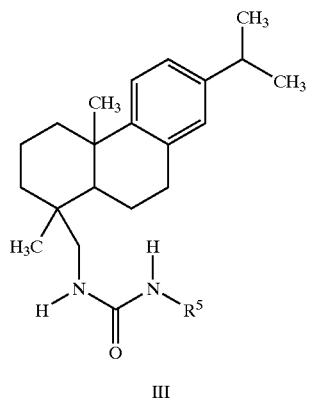

III

Scheme 3

Schiff-bases of Rosin amine are accessible via condensation of Rosin amine with an aldehyde or ketone (Houben-Weyl Vol. 11/2, 1958, 74–85).

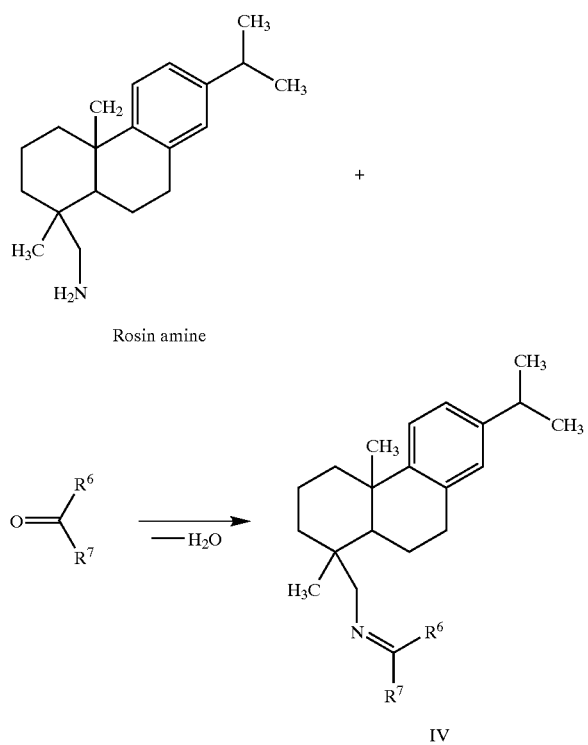

The synthesis of Rosin isocyanide has been published (T. Ohsawa et al., Tetrahedron Lett., 1989, 845–846).

Rosin isothiocyanate (CAS-Nr.: 115 269–93–7) can be synthesized from Rosin amine through reaction with thiophosgene (see analogous sequence with phosgene: Ozaki, Chem Rev. 72, 457–460), or alternatively with a thiophosgene substitute, namely thiocarbonyl-diimidazole (see example 3).

The preparation of Rosin isocyanate has been described (E. Corey et al., Tetrahedron Lett. 1981, 299–302).

In the case of compounds of formula 1 with n=0, the required starting material Dehydroabietan-1-yl-amine can be obtained according to Stockel et al., Can. J. Chem. 1963, 834–836.

The synthesis of Dehydroabietan-1-yl-isocyanate is described in Chem. Pharm. Bull. 1985, 1472–1487.

All other derivatives (formula I, n=0) can be synthesized in analogous manner as described for Rosin amine.

DETAILED DESCRIPTION OF THE PREFERRED EMBODIMENT

A fouling organism which may be combatted or controlled by the method of the invention can be any marine or freshwater organism which can attach to an inner or outer surface of a structure which is submerged or in continual contact with water. Examplary organisms include algae, including members of the phyla Chlorophyta, Pharophyta and Rhodophyta; tunicates, including members of the class Ascidiacea such as *Ciona intestinalis, Diplosoma listerianium* and *Botryllus sclosseri*, and members of the class Hydrozoa including *Clava squamata, Hydractinia echinata, Obelia geniculata* and *Tubularia larynx*;

Bivalves including *Mytilus edulis, Cassostrea virginica, Ostrea edulis, ostrea chilensia, Lasaea rubra* and members of the family Dreissenidae (or zebra mussels) and members of the family Corbuculidae (or Asiatic clams), bryozoans including *Electra pilosa, Conopeum reticulatum, Bugula neritina* and *Bowerbankia gracilis*;

Polychaete worms including *Hydroides norvegica, Pomatoceros triqueter, Mercierella enigmata and Spirorbis* spp.;

Sponges and members of the class Cirripedia (barnacles) such as *Balanus amphitrite, Lepas anatifera, Balanus balanus, Balanus balanoides, Balanus hameri, Balanus creatus, Balanus improvisus, Balanus ga*/*eatus, Balanus eburneus, Elminius modestus, Balanus tulipiformis* and *Balanus perforatus*.

Organisms of the genus *Balanus* are frequent foulers of aquatic structures. Specific fouling organisms to which this invention is especially directed include barnacles, zebra mussels, algae, diatoms, hydroids, bryozoa, ascidians, tube worms and asiatic clams, but also the bacterial slime.

Among the aquatic structures which may be protected by the method of invention are any submerged or partially submerged structure, either mobile or stationary, such as fishnet, boat, ship, piling, cooling tower, pipeline, standpipe, heat exchanger, dam, intake screen or the like.

In actual practice compound of formula I1–I13 may be brought into contact with a fouling organism by:

coating the aquatic structure to be protected with an antifouling-effective amount of said Rosin Amine derivative such that the antifouling compound is released at the to be protected surface area into the aquatic environment immediately.

including an antifouling-effective amount of the Rosin Amine Derivative within material formed into an aquatic structure which then releases said compound, releasing an antifouling-effective amount of said compound directly into the aquatic environment surrounding the structure to be protected, or any other method wherein the Rosin Amine Derivative comes in contact with the fouling organism.

The amount of Rosin Amine Derivative to be used in the method of invention will vary according to the specific compound used, the identity of the fouling organism to be controlled, degree of fouling pressure of the surrounding aquatic environment, the water temperature, the mode of contact and the like.

The Rosinamine derivatives can be used as individual active compounds or else in combination with active compounds usually employed in the anti-fouling sector. These can preferably be heavy metals, such as Cu, or heavy metal compounds, such as, for example, bis(trialkyltin) sulphides, tri-n-butyl laurate, tri-n-butyl chloride, copper(I) oxide, triethyltin chloride, tri-n-butyl(2-phenyl-4-chlorophenoxy)-tin, tri-butylin oxide, molybdenum disulfide, antimony oxide, polymeric butyl titanate, phenyl-(bispyridine)-bismuth chloride, tri-n-butyltin fluoride, manganese ethylenebisdithiocarbamate, zinc dimethyldithiocarbamate, zinc ethylenebisdithiocarbamate, the zinc salt or copper salt of 2-pyridinethiol-1-oxide, bisdimethyldithiocarbamoyl-zinc ethylenebisdithiocarbamate, zinc oxide, copper(I) ethylene-bis-dithiocarbamate, copper thiocyanate, copper naphthenate and tributyltin halides.

The action spectrum of the rosinamine derivatives is extended further or particular effects are achieved by these combinations of active compounds. Synergistic effects are obtained in many cases. The synergistic effect manifests itself particularly clearly if the active compound combinations are present in certain weight ratios. However, the weight ratios of the active compounds in the active compound combinations can vary within a relatively wide range.

Preferred combination partners for the rosinamine derivatives are algicides, such as diuron, dichlorophen, endothal, fentin acetate or quinoclamine, molluscicides, such as fentin acetate, metaldehyde, methiocarb, niclosamide, thiodicarb and trimethacarb, fungicides, such as dichlofluanid, tolylfluanid, iodopropargyl butylcarbamate, fluorfolpet and azoles, such as propiconazole, metconazole, cyproconazole and tebuconazole or conventional antifouling active compounds, such as 2-(N,N-dimethylthiocarbamoylthio)-5-nitrothiazyl, tetrabutyldistannoxane, 2-tert-butylamino-4-cyclopropylamino-6-methylthio-1,3,5-triazine, 4,5-dichloro-2-n-octyl-4-isothiazolin-3-one, 2,4,5,6-tetrachloroisophthalodinitril, tetramethylthiuram disulphide, 2,4,6-trichloro-phenylmaleimide, 2,3,5,6-tetrachloro-4-(methylsulphonyl)-pyridine, diiodomethyl-paratryl sulphone, thiabendazol, tetraphenylboron-pyridin salt, and the copper and sodium salt of 2-pyridinethiol-1-oxide.

The anti-fouling composition preferably comprises the rosinamine derivatives in concentrations of 0.5 to 60% by weight, preferably between 1 to 25% by weight.

Compositions of the invention comprise an aquatically acceptable inert carrier and an antifouling-effective amount of a Rosin Amine Derivative of formula I. For application onto structural surfaces, preferred compositions of the invention include a film-forming component such as a polymer resin solution. Exemplary polymer resins include unsaturated polyester resins formed from: a) unsaturated acids or anhydrides, such as maleic anhydride, fumaric acid, itaconic acid and the like; b) saturated acids or anhydrides, such as phthalic anhydride, isophthalic anhydride, terephthalic anhydride, tetrahydrophthalic anhydride, tetrahalophthalic anhydride, adipic acid, subacic acid, and the like; c) glycols, such as ethylene glycol, and the like; d) vinyl monomers, such as styrene, vinyl toluene, chlorostyrene, bromostyrene, acrylates like methylmethacrylate, ethylene glycol dimethacrylate and the like. Other suitable resins include vinyl ester-, vinyl acetate-, and vinyl chloride-based resins, elastomeric components, vulcanized rubbers, rosins, metalresinates and urethane-based resins.

For further description of components common in anti-fouling paints see Ungerer in *Chem. Ind.* 1985, 37, 730–732 and Williams in *Antifouling Marine Coatings, Noves, Park Ridge,* 1973.

EXAMPLE 1

N-Formyl-rosinamine (1)

The starting material Rosinamine (Hercules® Amine D) is a mixture of primary amines derived from modified Rosin. It is described as dehydroabietylamine of technical grade and was used in the following syntheses without further purification.

To a solution of Rosin amine in ethyl acetate 5 equiv. of ethyl formate are added at room temperature under continuous stirring. After 16 h at rt, the solvent is evaporated to dryness and the residue is filtered through a short column of silica gel to furnish N-formyl rosin amine under the form of a compact resin (yield: 86%). Characterisation: visqueous oil; $^1$H-NMR, $\delta$(ppm): 7.94–8.23(1H); 7.15 (1H); 6.99 (1H); 6.89 (1H); 5.46 (1H); 2.76–3.27 (5H); 1.22 (6H); 1.21 (3H); 0.95 (3H).

EXAMPLE 2

Rosin Isocyanide (2)

Diisopropylarine (2.7 equiv.) and phosphorous oxychloride (1.1 equiv.) were successively added dropwise to a stirred solution of N-formyl rosinamine in dichloromethane at 0° C. under an atmosphere of dry nitrogen. After 1 h at 0° C., a 20% solution of sodium carbonate was added and the reaction mixture was allowed to reach room temperature for 1 h. 20% sodium carbonate and water were added, extraction of the aqueous phase with dichloromethane followed by filtration of the residue through a column of silica gel furnished Rosin isocyanide as a colourless oil (yield: 85%).

Characterisation: visqueous oil; $^1$H NMR, $\delta$(ppm): 7.16 (1H); 7.00 (1H); 6.88 (1H); 2.76–3.34 (5H); 1.22 (6H); 1.21 (3H); 0.98 (3H).

EXAMPLE 3

Rosin Isothiocyanate (3)

A solution of thiocarbonyl diimidazole (1.5 equiv.) in dichloromethane was added to a stirred solution of Rosinamine in dichloromethane at 0° C. under an atmosphere of dry nitrogen. After the addition was complete, the reaction mixture was heated at 45° C. during 16 h. The solvent was evaporated and the solid residue filtered through a column of silica gel to furnish Rosinisothiocyanate as an oil (yield: 87%). Characterisation: oil; $^1$H-NMR, $\delta$(ppm): 7.16 (1H); 6.99 (1H); 6.89 (1H); 3.37 (2H); 2.90 (2H); 2.82 (1H); 1.22 (6H); 1.21 (3H); 0.96 (3H).

Evaluation of Marine Antifouling Activity of Test Compounds

The rate of settlement of laboratory reared cyprid larvae of the barnacle Balanus amphitrite was determined for testing the activity of candidate anti-fouling compounds.

Settlement Assay

Tests are carried out in four replicates in sterile polystyrene multi well plates. Between 25 and 40 cyprid larvae are injected in the dishes containing either 2 ml of test solution (see below), solvent control or a positive control (Dichloro-n-octyl-isothiazolinone).

Dishes are incubated for 24 h at a temperature of 27° C.±2. After incubation the cyprids are screened for signs of toxicity. Larvae are classified in three categories: A) alive and swimming; B) alive but not active; C) dead. The test is terminated by addition of a drop of 20% formaldehyde and the numbers of settled and non-settled larvae are counted.

Settlement is evaluated as follows: 1) Non settled: not attached free swimming cyprids; 2) settled cyprids: attached, but not metamorphosed cyprids; 3) barnacles: attached juvenile barnacles.

Categories 2 and 3 are considered to be settled. Percentage settlement in test solution is compared with controls. Estimates of the median effect concentration (EC-50) after 50 hrs. are calculated using the Spearman-Kärber method.

All seawater used is of natural origin and filtered unto 0.2 micron. Stock solutions of test compounds are prepared by dissolving an amount of test substance in a suitable solvent and subsequent addition of seawater.

The stock solutions are used to prepare several dilution series in seawater. Controls are made of seawater, or, if appropriate, in a mixture of seawater and solvent. The solvent concentration in the controls is equal to the highest concentration in the test solution. As an internal standard (positive control) a concentration range of 0 to 5 ppm dichloro-n-octylisothiazolinone will is included in each test.

| Test Results | |
|---|---|
| Compound | EC50 for settlement inhibition in ppm |
| 1 | 2.6 |
| 2 | 0.12 |
| reference* | 0.37 |

*= 4,5-dichloro-n-octylisothiazolinone

What is claimed is:

1. A compound selected from the group consisting of compounds having the formulae 11, 12, 13, 15, 16, 17, 18, 19, 110, 111, 112, and 113:

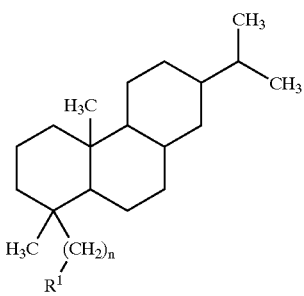

I1

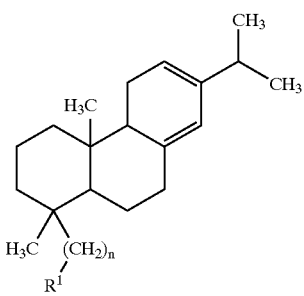

I2

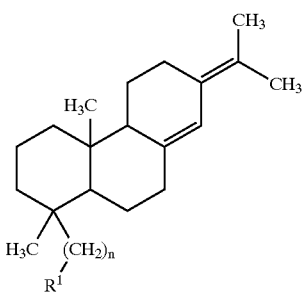

I3

-continued

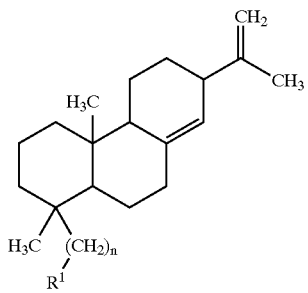

I5

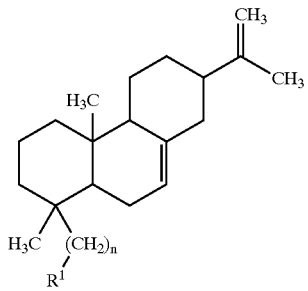

I6

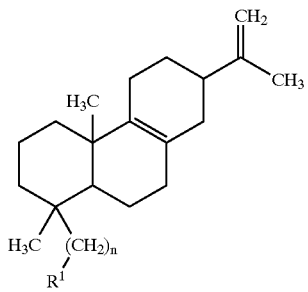

I7

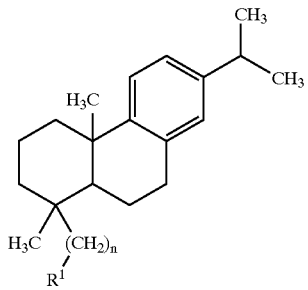

I8

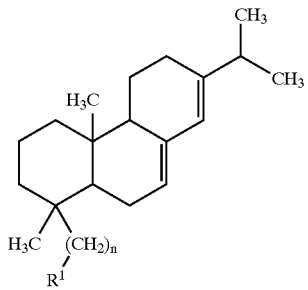

I9

-continued

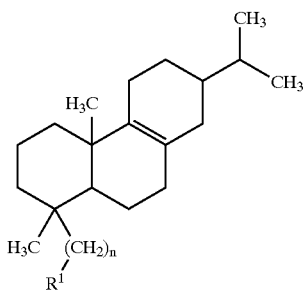

I10

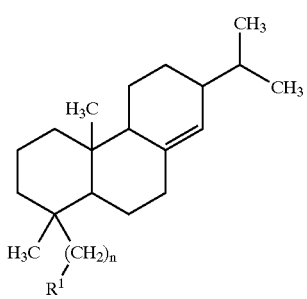

I11

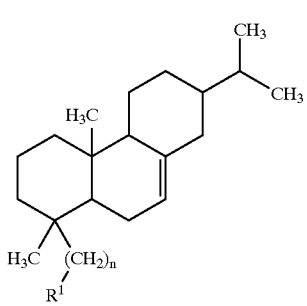

I13 wherein
$R^1$ represents $NR^2R^3$ wherein
  $R^2$ represents a hydrogen atom or a C1–C8-alkyl and
  $R^3$ represents $C=OR^4$ wherein
    $R^4$ represents a hydrogen atom or one of the groups $OR^5$ or $NHR^5$ wherein
      $R^5$ designates a C1–C8-alkyl or aryl, each optionally substituted by halogen; or
$R^1$ represents $N=CR^6R^7$ wherein
  $R^6$ represents a hydrogen atom or a C1–C6-alkyl or aryl, and
  $R^7$ represents a C1–C6-alkyl or aryl, each optionally substituted by halogen; or
$R^1$ represents an isonitrile, isocyanate, isothiocyanate or guanidino group; and
  n represents 0 or 1 and wherein when $R^1$ is isothiocyanate, n is 0.

2. The compound according to claim 1, wherein $R^1$ represents $NR^2R^3$, and wherein
  $R^2$ represents a hydrogen atom or a C1–C4-alkyl and
  $R^3$ represents $C=OR^4$ wherein
    $R^4$ represents a hydrogen atom or one of the groups $OR^5$ or $NHR^5$ wherein
      $R^5$ represents a C1–C4-alkyl or aryl, each optionally substituted by halogen; or
$R^1$ represents $N=CR^6R^7$ wherein
  $R^6$ represents a hydrogen atom, methyl or optionally halogen substituted aryl, and
  $R^7$ represents a C1–C4-alkyl or optionally halogen substituted aryl; or $R^1$ represents an isonitrile, isocyanate, isothiocyanate or guanidino moiety.

3. The compound according to claim 1, wherein
$R^1$ represents $NR^2R^3$ wherein
  $R^2$ represents a hydrogen atom and
  $R^3$ represents $C=OR^4$ wherein
    $R^4$ represents a hydrogen atom.

4. The composition according to claim 1, wherein
$R^1$ represents $NR^2R^3$ wherein
  $R^2$ represents a hydrogen atom or a C1—C4-alkyl and
  $R^3$ represents $C=OR^4$ wherein
    $R^4$ represents a hydrogen atom or one of the groups $OR^5$ or $NHR^5$ wherein
      $R^5$ represents a C1—C4-alkyl or aryl, each optionally substituted by halogen; or
$R^1$ represents $N=CR^6R^7$ wherein
  $R^6$ represents a hydrogen atom, methyl or optionally halogen substituted aryl, and
  $R^7$ represents a C1–C4-alkyl optionally halogen substituted aryl; or
$R^1$ represents an isonitrile, isocyanate, isothiocyanate or guanidino moiety.

5. A method for controlling or combatting a marine or freshwater fouling organism comprising contacting said organism or the locus thereof with an anti-fouling-effective amount of at least one selected from the group consisting of compounds having the formulae 11, 12, 13,, 15, 16, 17, 18, 19, 110, 111, 112, and 113:

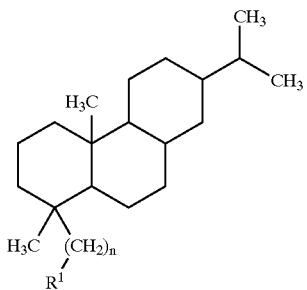

I1

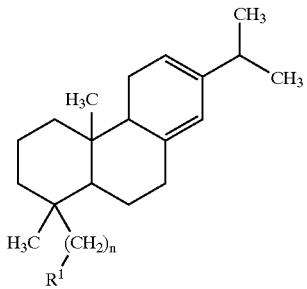

I2

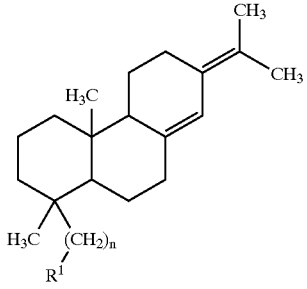

I3

-continued

I5
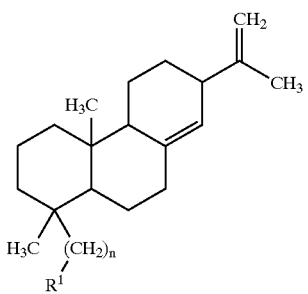

I6
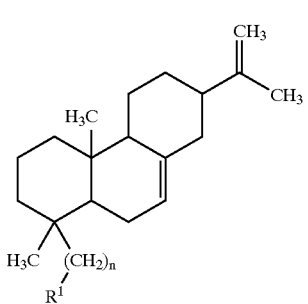

I7
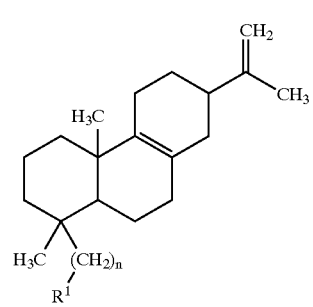

I8
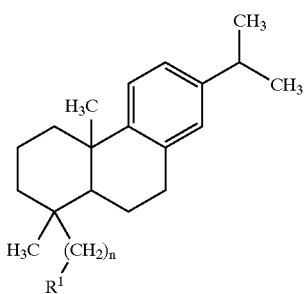

I9
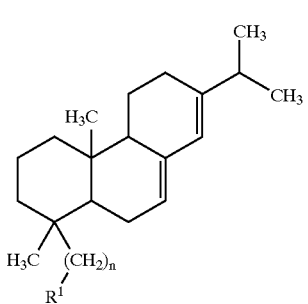

-continued

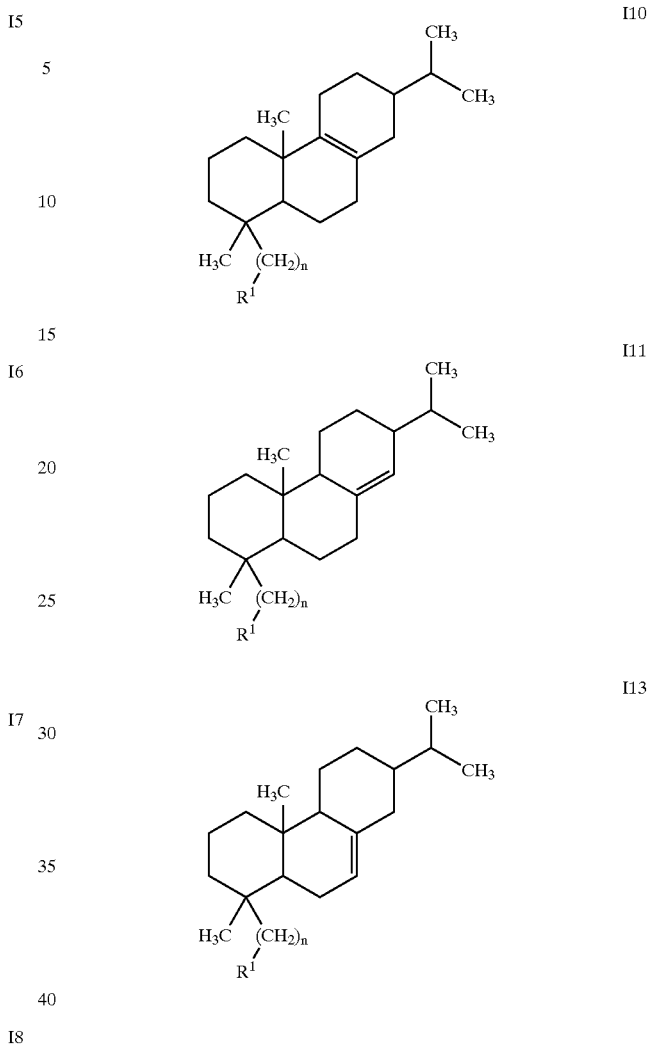

wherein
R¹ represents NR²R³ wherein
R² represents a hydrogen atom or a C1–C8-alkyl and
R³ represents C=OR⁴ wherein
R⁴ represents a hydrogen atom or one of the groups OR⁵ or NHR⁵ wherein
R⁵ designates a C1–C8-alkyl or aryl, each optionally substituted by halogen; or
R¹ represents N=CR⁶R⁷ wherein
R⁶ represents a hydrogen atom or a C1–C6-alkyl or aryl, and
R⁷ represents a C1–C6-alkyl or aryl, each optionally substituted by halogen; or
R¹ represents an isonitril, isocyanate, isothiocyanate or guanidino group; and
n represents 0 or 1.

6. An agent comprising an antifouling-effective amount of at least one compound and an aquatically acceptable inert carrier, wherein the compound is selected from the group consisting of compounds having the formulae 11, 12, 13, 15, 16, 17, 18, 19, 110, 111, 112, and 113:

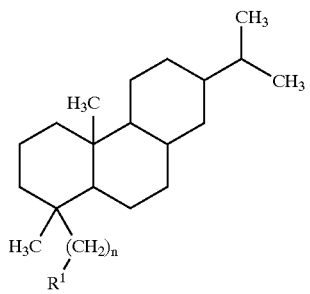
I1
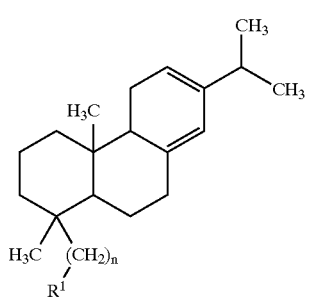
I2
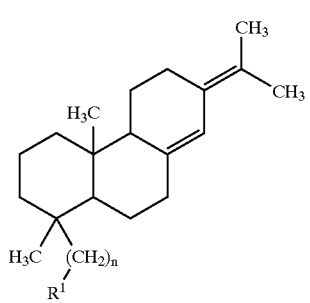
I3
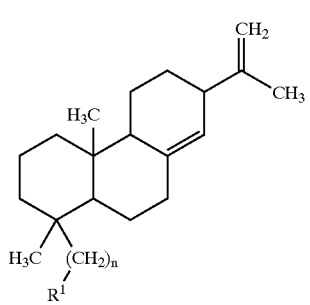
I5
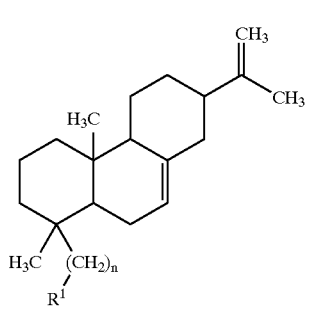
I6
-continued
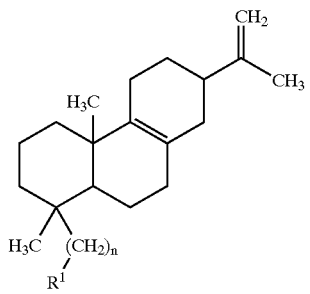
I7
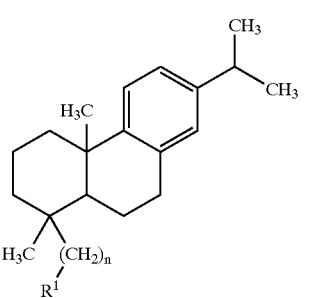
I8
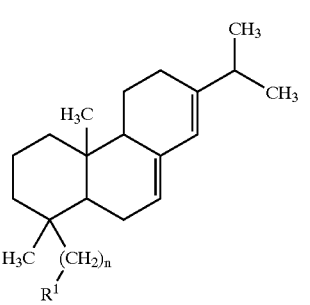
I9
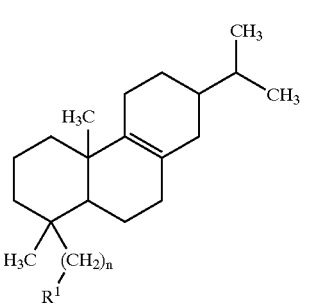
I10
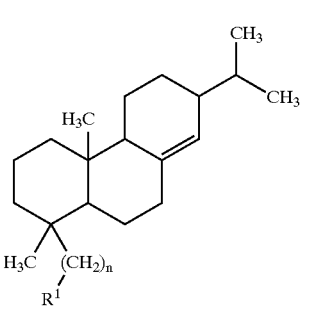
I11

-continued

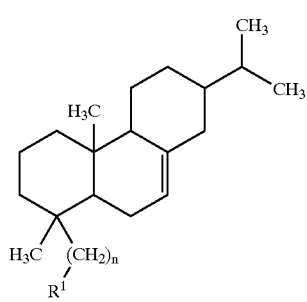

I13 wherein
R$^1$ represents NR$^2$R$^3$ wherein
R$^2$ represents a hydrogen atom or a C1–C8-alkyl and
R$^3$ represents C=OR$^4$ wherein
R$^4$ represents a hydrogen atom or one of the groups OR$^5$ or NHR$^5$, wherein
R$^5$ designates a C1–C8-alkyl or aryl, each optionally substituted by halogen; or
R$^1$ represents N=CR$^6$R$^7$ wherein
R$^6$ represents a hydrogen atom or a C1–C6-alkyl or aryl, and
R$^7$ represents a C1—C6-alkyl or aryl, each optionally substituted by halogen; or
R$^1$ represents an isonitril, isocyanate, isothiocyanate or guanidino group; and
n represents 0 or 1.

7. The agent of claim 6, wherein the agent comprises 0.5 to 60% by weight of said compound.

8. A method for controlling and combatting a marine fouling organism, a freshwater fouling organism, or combinations thereof,
the method comprising treating the organism with a compound selected from the group consisting of compounds having the formulae 11, 12, 13, 15, 16, 17, 18, 19, 110, 111, 112, and 113:

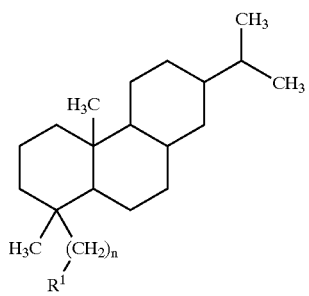

I1

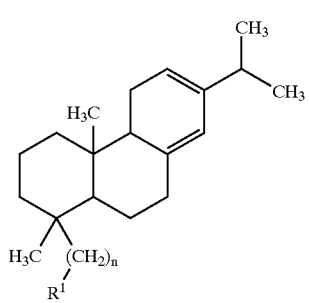

I2

-continued

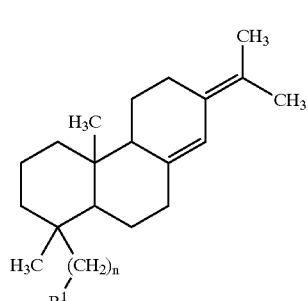

I3

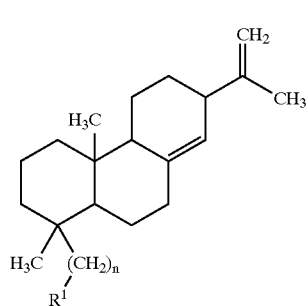

I5

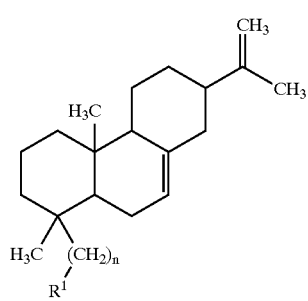

I6

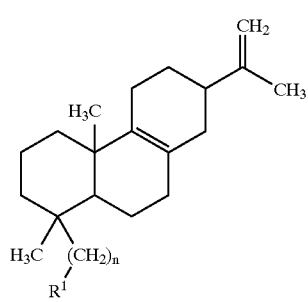

I7

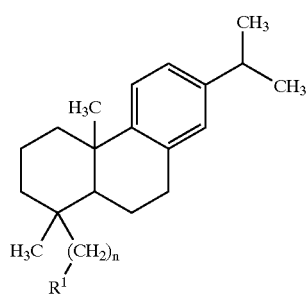

I8

-continued

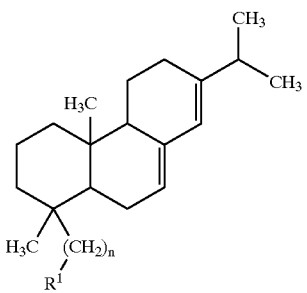
I9

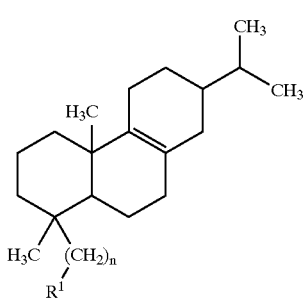
I10

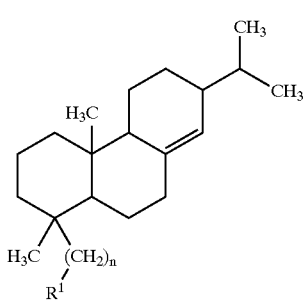
I11

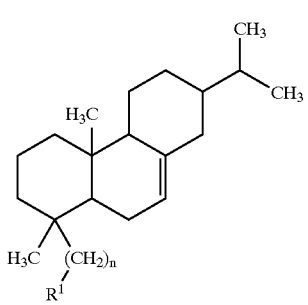
I13 wherein
$R^1$ represents $NR^2R^3$ wherein
  $R^2$ represents a hydrogen atom or a C1–C8-alkyl and
  $R^3$ represents $C=OR^4$ wherein
    $R^4$ represents a hydrogen atom or one of the groups $OR^5$ or $NHR^5$ wherein
      $R^5$ designates a C1—C8-alkyl or aryl, each optionally substituted by halogen; or
$R^1$ represents $N=CR^6R^7$ wherein
  $R^6$ represents a hydrogen atom or a C1–C6-alkyl or aryl, and
  $R^7$ represents a C1–C6-alkyl or aryl, each optionally substituted by halogen; or
$R^1$ represents an isonitril, isocyanate, isothiocyanate or guanidino group; and
n represents 0 or 1.

9. The method of claim 8, wherein the organism is treated with an agent comprising an antifouling-effective amount of the compound and an aquatically acceptable inert carrier.

10. A process for preparing an anti-fouling agent comprising mixing a compound with an aquatically acceptable inert carrier, wherein the compound is selected from the group consisting of compounds having the formulae 11, 12, 13, 15, 16, 17, 18, 19, 110, 111, 112, and 113:

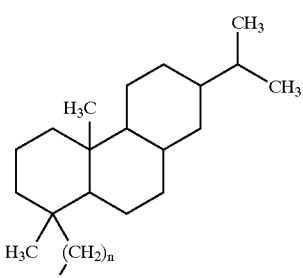
I1

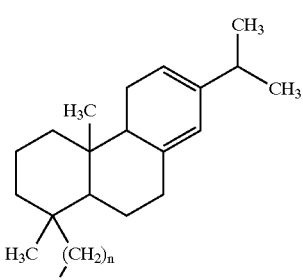
I2

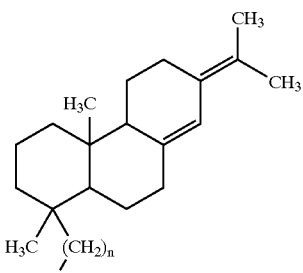
I3

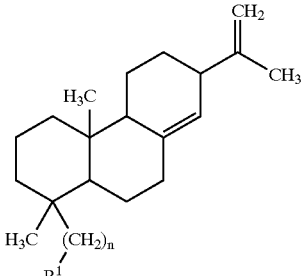
I5

-continued

I6
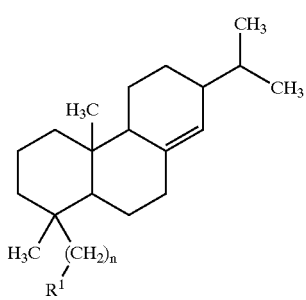

I7
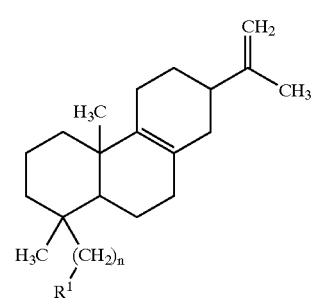

I11
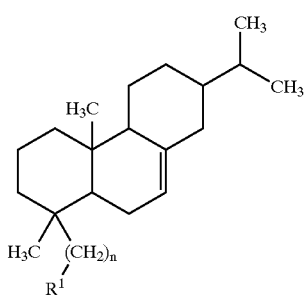

I13
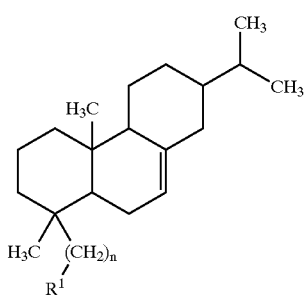

wherein
R¹ represents NR²R³ wherein
R² represents a hydrogen atom or a C1–C8-alkyl and
R³ represents C=OR⁴ wherein
R⁴ represents a hydrogen atom or one of the groups OR⁵ or NHR⁵ wherein
R⁵ designates a C1–C8-alkyl or aryl, each optionally substituted by halogen; or
R¹ represents N=CR⁶R⁷ wherein
R⁶ represents a hydrogen atom or a C1–C6-alkyl or aryl, and
R⁷ represents a C1—C6-alkyl or aryl, each optionally substituted by halogen; or
R¹ represents an isonitril, isocyanate, isothiocyanate or guanidino group; and
n represents 0 or 1.

11. An agent comprising an antifouling-effective amount of at least one compound and a film forming polymer resin, wherein the compound is selected from the group consisting of compounds of claim 1 having the formulae 11, 12, 13, 15, 16, 17, 18, 19, 110, 111, 112, and 113:

I8
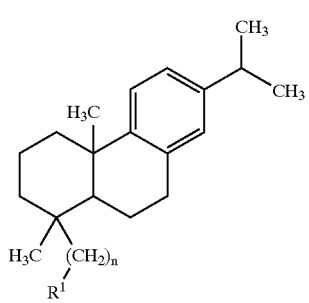

I9
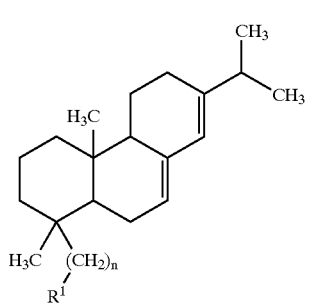

I10
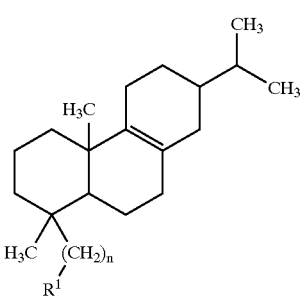

I1
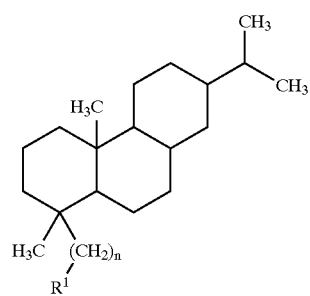

-continued
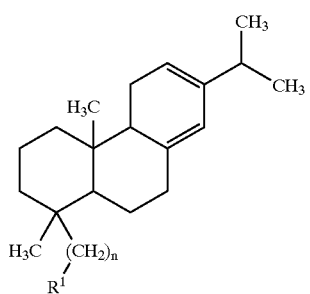
I2
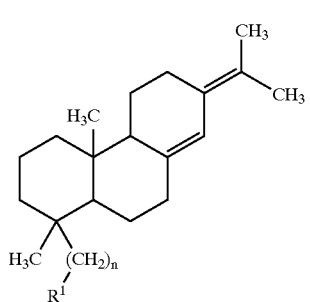
I3
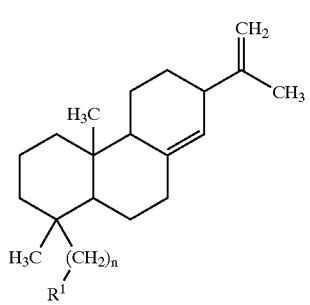
I5
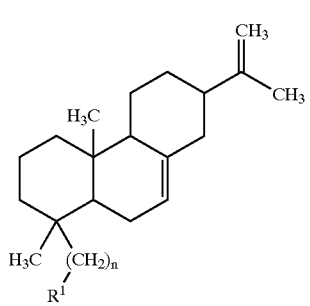
I6
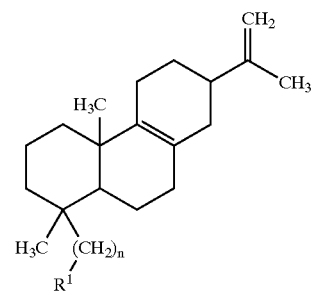
I7
-continued
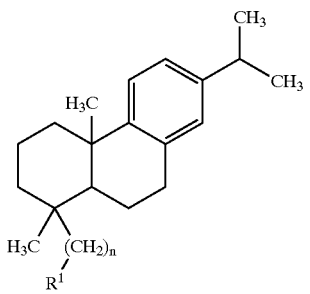
I8
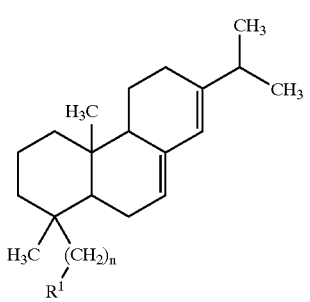
I9
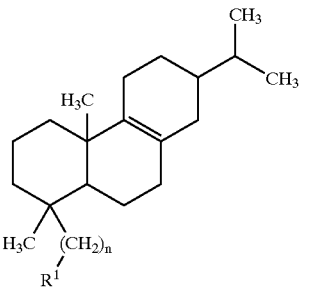
I10
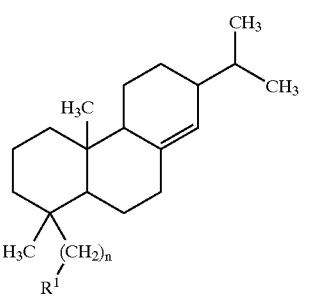
I11
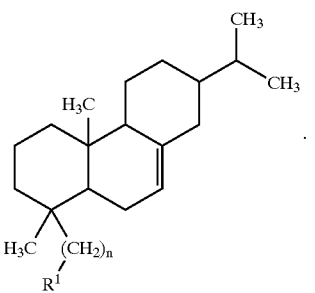
I13

12. The agent of claim 11 wherein, the polymer is selected from the group consisting of unsaturated polyester resins formed from monomers comprising: a) unsaturated acids or anhydrides, selected from the group consisting of maleic anhydride, fumaric acid, itaconic acid and admixtures thereof; b) saturated acids or anhydrides, selected from the group consisting of phthalic anhydride, isophthalic anhydride, terephthalic anhydride, tetrahydrophthalic anhydride, tetrahalophthalic anhydride, adipic acid, subacic acid, and admixtures thereof, c) glycols, selected from the group consisting of ethylene glycol, and the like; d) vinyl monomers, selected from the group consisting of styrene, vinyl toluene, chlorostyrene, bromostyrene, acrylates selected from the group consisting of methylmethacrylate, ethylene glycol dimethacrylate and admixtures thereof vinyl ester-, vinyl acetate-, and vinyl chloride-based resins; elastomeric components; vulcanized rubbers; rosins; metalresinates; and urethane-based resins.

13. An agent comprising an antifouling-effective amount of at least one compound and an algicide, wherein the compound is selected from the group consisting of compounds of claim 1 having the formulae 11, 12, 13, 15, 16, 17, 18, 19, 110, 111, 112, and 113:

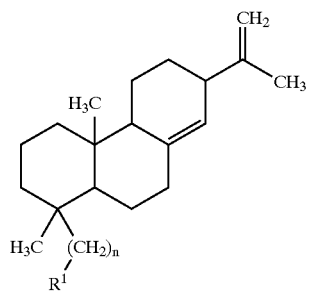

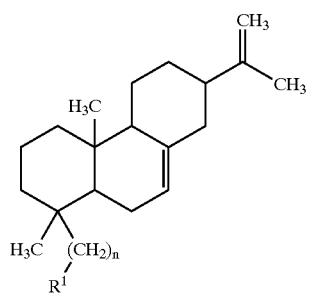

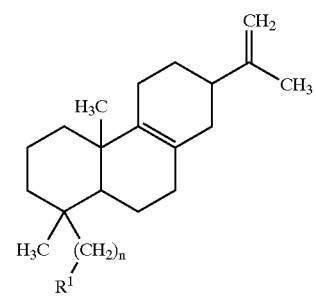

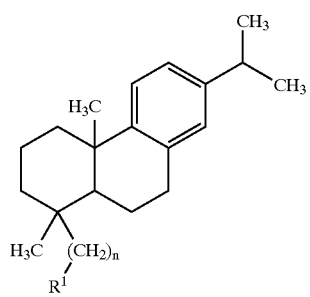

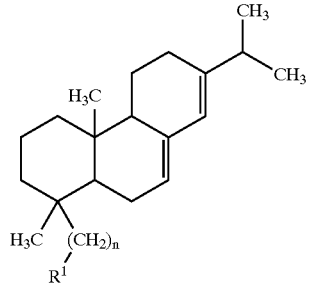

-continued

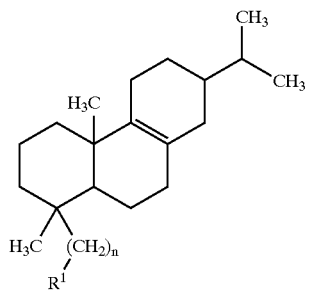

I10

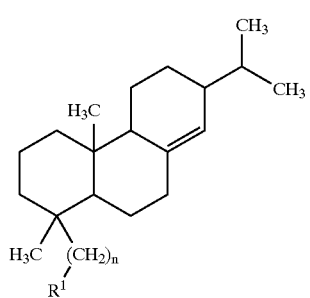

I11

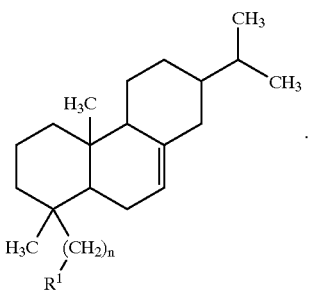

I13

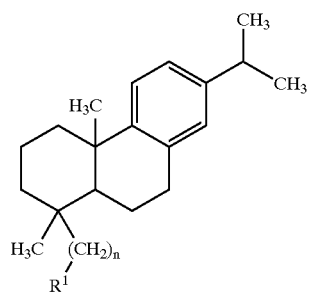

I8 wherein
R¹ represents NR²R³ wherein
R² represents a hydrogen atom or a C1—C8-alkyl and
R³ represents C=OR⁴ wherein
R⁴ represents a hydrogen atom or one of the groups OR⁵ or NHR⁵ wherein
R⁵ designates a C1–C8-alkyl or aryl, each optionally substituted by halogen; or
R¹ represents N=CR⁶R⁷ wherein
R⁶ represents a hydrogen atom or a C1–C6-alkyl or aryl, and
R⁷ represents a C1–C6-alkyl or aryl, each optionally substituted by halogen; or
R¹ represents an isonitrile, isothiocyanate or guanidino group; and
n represents 0 or 1; or when
R¹ is isothiocyanate or isonitrile, then n is 0.

16. A compound selected from the group consisting of compounds having the formulae 11, 12, 13, 15, 16, 17, 19, 110, 111, 112, and 113:

14. The agent of claim 13, where in the algicide is selected from the group consisting of diuron, dichlorophen, endothal, fentin acetate or quinoclamine, molluscicides, selected from the group consisting of fentin acetate, metaldehyde, methiocarb, niclosamide, thiodicarb and trimethacarb, fungicides, selected from the group consisting of dichlofluanid, tolylfluanid, iodopropargyl butylcarbamate, fluorfolpet and azoles, selected from the group consisting of propiconazole, metconazole, cyproconazole and tebuconazole and antifouling active compounds, selected from the group consisting of 2-(N,N-dimethylthiocarbamoylthio)-5-nitrothiazyl, tetrabutyldistannoxane, 2-tert-butylamino-4-cyclopropylamino-6-methyl-thio-1,3,5-triazine, 4,5-dichloro-2-n-octyl-4-isothiazolin-3-one, 2,4,5,6-tetrachloroisophthalodinitril, tetramethylthiuram disulphide, 2,4,6-trichlorophenylmaleimide, 2,3,5,6-tetrachloro-4-(methylsulphonyl)-pyridine, diiodomethyl-paratryl sulphone, thiabendazol, tetraphenylboron-pyridin salt, and the copper and sodium salt of 2-pyridinethiol-1-oxide.

15. A compound selected from the group consisting of compounds having the formula 18,:

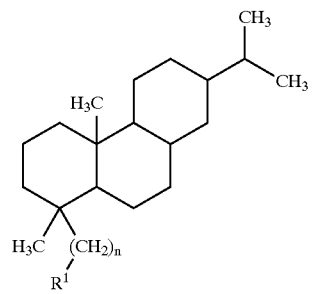

I1

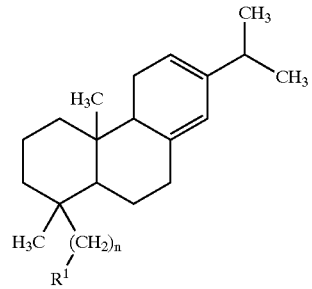

I2

-continued

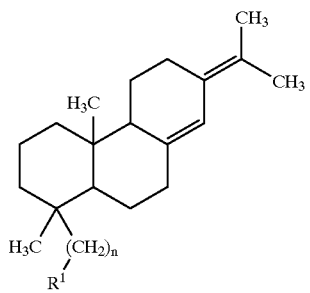
I3

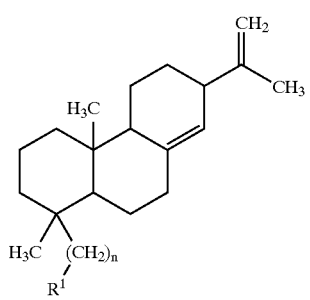
I5

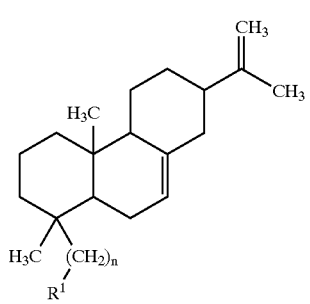
I6

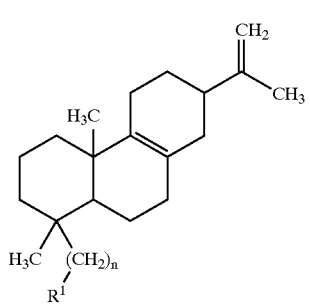
I7

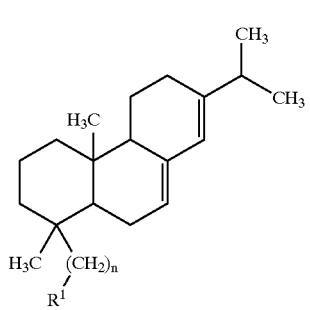
I9

-continued

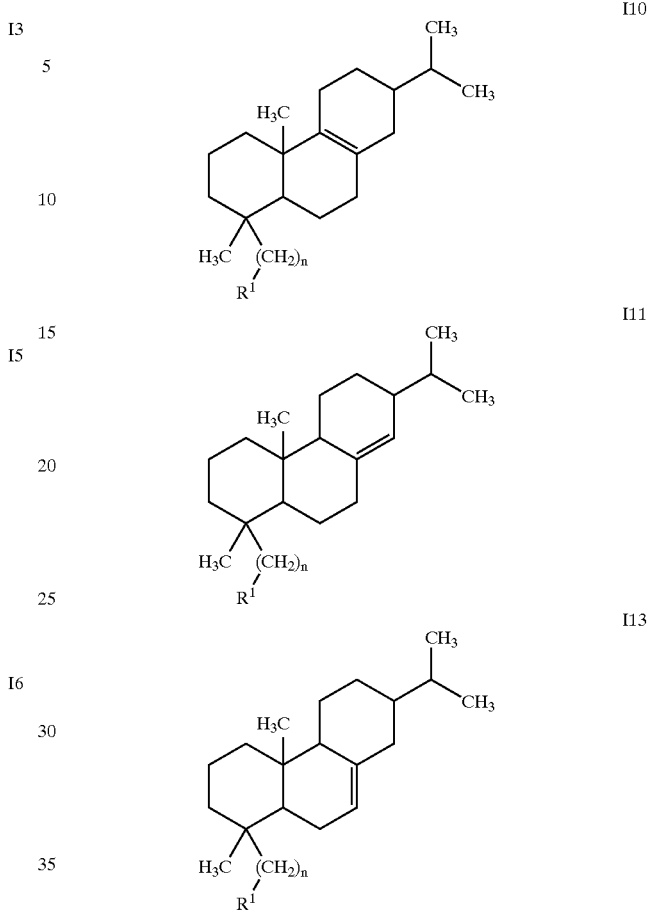

wherein
  $R^1$ represents $NR^2R^3$ wherein
    $R^2$ represents a hydrogen atom or a C1—C8-alkyl and
    $R^3$ represents $C=OR^4$ wherein
    $R^4$ represents a hydrogen atom or one of the groups $OR^5$ or $NHR^5$ wherein
    $R^5$ designates a C1–C8-alkyl or aryl, each optionally substituted by halogen; or
  $R^1$ represents $NR^2R$ wherein
    $R^2$ represents a C1–C8-alkyl and
    $R^3$ represents $C=OR^4$ wherein
    $R^4$ represents a hydrogen atom or one of the groups $OR^5$ or $NHR^5$ wherein
    $R^5$ designates a C1–C8-alkyl or aryl, each optionally substituted by halogen; or
  $R^1$ represents $N=CR^6R^7$ wherein
    $R^6$ represents a hydrogen atom or a $C_1$–$C_6$-alkyl or aryl, and
    $R^7$ represents a C1–C6-alkyl or aryl, each optionally substituted by halogen; or
  $R^1$ represents an isonitrile, -isocyanate, isothiocyanate or guanidino group; and
  n represents 0 or 1;
    wherein when the formula is 11, and R1 is isocyanate or isothiocyanate then n=1.

* * * * *